United States Patent [19]

Nomura

[11] Patent Number: 5,203,333
[45] Date of Patent: Apr. 20, 1993

[54] ACOUSTIC WAVE THERAPY APPARATUS

[75] Inventor: Satoshi Nomura, Ootawara, Japan

[73] Assignee: Kabushiki Kaisha Toshiba, Kawasaki, Japan

[21] Appl. No.: 931,497

[22] Filed: Aug. 21, 1992

Related U.S. Application Data

[63] Continuation of Ser. No. 745,951, Aug. 12, 1991, abandoned, which is a continuation of Ser. No. 522,322, May 11, 1990, abandoned.

[30] Foreign Application Priority Data

May 15, 1989 [JP] Japan ................................. 1-121207

[51] Int. Cl.⁵ ............................................ A61B 17/22
[52] U.S. Cl. ............................ 128/660.03; 128/24 EL; 128/804
[58] Field of Search ........ 128/24 AA, 24 EL, 660.03, 128/804

[56] References Cited

U.S. PATENT DOCUMENTS 4,811,725  3/1989  Grasser ......................... 128/24 EL
4,928,672  5/1990  Grasser et al. ..................... 128/24

FOREIGN PATENT DOCUMENTS

296349 12/1988 European Pat. Off. .
301198  2/1989 European Pat. Off. .
3532184  2/1987 Fed. Rep. of Germany .

Primary Examiner—Ruth S. Smith
Attorney, Agent, or Firm—Foley & Lardner

[57] ABSTRACT

In an acoustic wave therapy apparatus, irradiation devices for generating acoustic waves for medical treatment are arranged on one side of a holder. A water bag is provided on the one side of the holder. The water bag is put in contact with the surface of a subject. A probe rod is arranged within the water bag advanceably and retractably through a through-hole formed in the holder. An ultrasonic probe for ultrasonic tomographic imaging is provided at an end portion of the probe rod. The probe rod has a rack gear. A pinion gear engaged with the rack gear, a drive shaft for driving the pinion gear, and a bearing seat for receiving the drive shaft are arranged on the other side of the holder. This apparatus is further provided with a pressing force maintaining device for limiting to a predetermined value the pressing force with which the end portion of the probe rod is pressed on the surface of the subject via the water bag, and a retracting device for retracting the probe rod when the end portion of the probe rod receives a predetermined upward force from the surface of the subject via the water bag. This apparatus can treat calculi and cancerous cells, while ensuring the safety for the subject.

16 Claims, 6 Drawing Sheets

PRIOR ART

ACOUSTIC WAVE THERAPY APPARATUS

This application is a continuation of application Ser. No. 07/745,951, filed Aug. 12, 1991, now abandoned, which is a continuation of application Ser. No. 07/522,322, filed May 11, 1990, now abandoned.

BACKGROUND OF THE INVENTION

1. Field of the Invention

The present invention relates generally to an acoustic wave therapy apparatus for treating cancerous cells or calculi in a human body, using shock waves produced by acoustic waves or continuous acoustic waves, and more particularly to an ultrasonic shock wave lithotripsy apparatus and an ultrasonic continuous wave hyperthermic therapy apparatus.

2. Description of the Related Art

Conventional ultrasonic treatment apparatuses include an ultrasonic shock wave lithotripsy apparatus for breaking calculi, etc. in a human body, using shock waves due to focusing ultrasonic energy, and an ultrasonic continuous wave hyperthermic therapy apparatus for treating a tumor by heating it up to a lethal temperature, using continuous focusing ultrasonic energy.

This type of ultrasonic treatment apparatus generally has an acoustic wave generator for generating ultrasonic waves. The acoustic wave generator has a concave surface for focusing the generated ultrasonic waves. The acoustic wave generator is arranged to face a subject, with a bag interposed therebetween. An ultrasonic imaging probe is arranged within the bag, for positioning the acoustic wave generator and for obtaining tomograms of the subject for confirming the result of treatment.

If a large-diameter acoustic wave generator is employed in this apparatus and generated waves are focused onto a region-of-interest (ROI), a maximum treatment effect is attained with a small treatment energy. In this case, however, if the focus of waves departs from the ROI, a normal tissue is damaged. It is thus important to precisely focus the waves onto the ROI.

Figure 1:
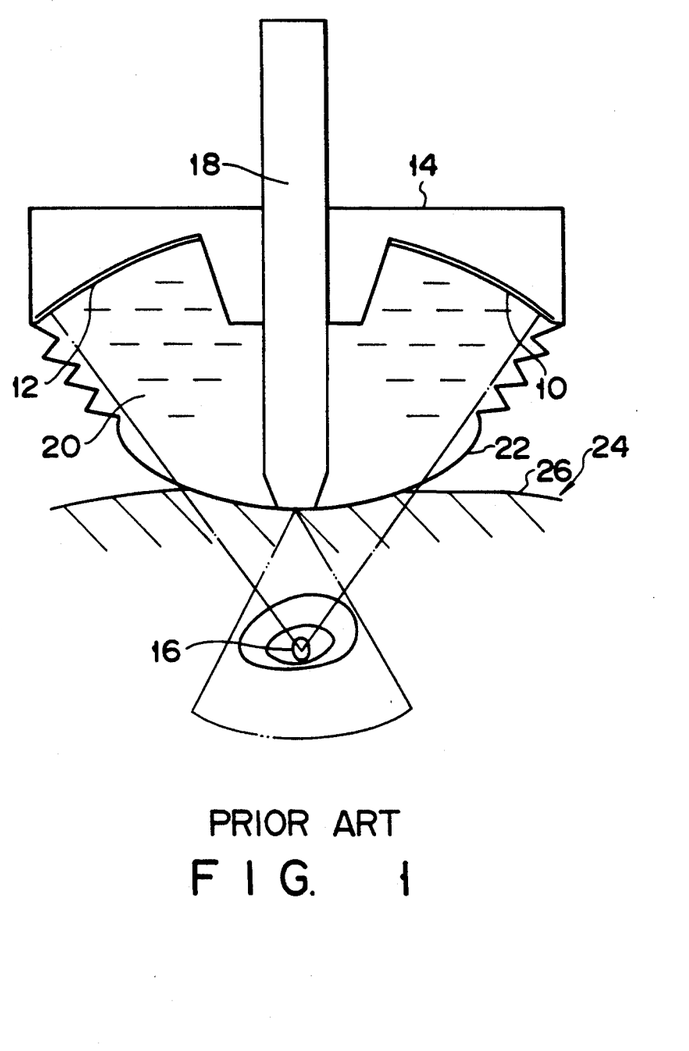
FIG. 1 is a cross-sectional view schematically showing a structure of a conventional acoustic wave therapy apparatus.

FIG. 1 is a cross-sectional view schematically showing an acoustic wave therapy apparatus having this type of imaging means. In FIG. 1, irradiation devices (as the acoustic wave generator) 10 and 12 serving as acoustic wave generators are secured to a holder 14. The irradiation devices 10 and 12 are arranged symmetrically with respect to an ultrasonic imaging probe 18 (described later) so that the focal points of the devices 10 and 12 may be positioned at a region-of-interest (ROI) 16. The acoustic wave therapy apparatus has a bag member 22 containing water 20 which is put in close contact with a surface 26 of a subject 24. The ultrasonic imaging probe 18 is arranged at the center of the holder 14 and is employed for effecting positioning for treatment and for receiving ultrasonic waves reflected from the ROI 16, thereby confirming if the ROI 16 has been treated appropriately. In FIG. 1, a dot-and-dash line indicates a region where ultrasonic waves for treatment are radiated, and a two-dot-and-dash line indicates a region where ultrasonic waves for ultrasonic imaging treatment are radiated.

When an acoustic wave therapy is performed by this apparatus, ultrasonic waves are radiated onto the ROI 16 in the subject 24 and the ultrasonic imaging probe 18 receives the waves reflected by the ROI 16. Tomograms are formed on the basis of the reflected waves, and the formed tomograms are displayed. Observing the tomograms, an operator moves and positions the apparatus so that the focal points of the irradiation devices 10 and 12 coincide with the location of the ROI 16. When the focal points of the devices 10 and 12 coincide with the location of the ROI 16, the devices 10 and 12 are driven to radiate intense ultrasonic waves onto the ROI 16, thereby treating the ROI 16.

As has been stated above, the ultrasonic imaging probe 18 is put on the surface 26 of the subject 24 via the water bag 22, manually or by means of an electric mechanism, thereby focusing the waves radiated from the devices 10 and 12 at the ROI 16 and confirming the result of treatment.

In the above-described prior art, however, the operator is unable to sense the intensity of the pressure under which the imaging probe 18 is pressed on the subject 24. Thus, if the operator presses the imaging probe 18 under high pressure for obtaining better tomograms, there is a concern that the subject may be injured.

SUMMARY OF THE INVENTION

The object of the present invention is to provide an acoustic wave therapy apparatus ensuring safety for a subject undergoing treatment.

According to one aspect of the invention, there is provided an acoustic wave therapy apparatus comprising: a holder having a concave surface at least on one side thereof, and also having a through-hole at its central portion; acoustic wave generating means, provided on one side of the holder, for generating acoustic waves for medical treatment; a bag member arranged on the one side of the holder and designed to be put in contact with the surface of a subject, and containing an acoustic wave propagation medium; a rod member inserted into the through-hole of the holder and arranged vertically movable in the bag member; an ultrasonic probe for ultrasonic wave tomographic imaging, provided at the bag member-side end portion of the rod member; a drive mechanism for vertically moving the ultrasonic probe relative to the holder; and a pressing force maintaining means arranged on the other side of the holder, for limiting to a predetermined value the pressing force with which the end portion of the rod member is pressed on the surface of the subject via the bag member.

According to another aspect of the invention, there is provided an acoustic wave therapy apparatus comprising: a holder having a concave surface at least on one side thereof, and also having a through-hole at its central portion; an acoustic wave generating means provided on one side of the holder for generating acoustic waves for medical treatment; a bag member arranged on the one side of the holder and designed to be put in contact with the surface of a subject, and containing an acoustic wave propagation medium; a rod member inserted into the through-hole of the holder and arranged vertically movable in the bag member; an ultrasonic probe for ultrasonic wave tomographic imaging, provided at the bag member-side end portion of the rod member; a drive mechanism for vertically moving the ultrasonic probe relative to the holder; and retracting means, arranged on the other side of the holder, for retracting the rod member when the end portion of the rod member receives a predetermined upward force from the surface of the subject via the bag member.

According to still another aspect of the invention, there is provided an acoustic wave therapy apparatus comprising: a holder having a concave surface at least on one side thereof, and also having a through-hole at its central portion; acoustic wave generating means, provided on one side of the holder, for generating acoustic waves for medical treatment; a bag member arranged on the one side of the holder and designed to be put in contact with the surface of a subject, and containing an acoustic wave propagation medium; a rod member inserted into the through-hole of the holder and arranged advanceably and retractably in the bag member; an ultrasonic probe for ultrasonic wave tomographic imaging, provided at the bag member-side end portion of the rod member; a drive mechanism for vertically moving the ultrasonic probe relative to the holder; pressing force maintaining means, arranged on the other side of the holder, for limiting to a predetermined value the pressing force with which the end portion of the rod member is pressed on the surface of the subject via the bag member; and retracting means, arranged on the other side of the holder, for retracting the rod member when the end portion of the rod member receives a predetermined upward force from the surface of the subject via the bag member.

According to still another aspect of the invention, there is provided an acoustic wave therapy apparatus comprising: a holder having a concave surface at least on one side thereof, and also having a through-hole at its central portion; acoustic wave generating means provided on one side of the holder, for generating acoustic waves for medical treatment; a bag member arranged on the one side of the holder and designed to be put in contact with the surface of a subject, and containing a acoustic wave propagation medium; a rod member inserted into the through-hole of the holder and arranged advanceably and retractably in the bag member; an ultrasonic probe for ultrasonic wave tomographic imaging, provided at the bag member-side end portion of the rod member; a rack gear provided on the rod member along its longitudinal direction; a pinion gear engaged with the rack gear; a drive shaft for driving the pinion gear; a bearing seat arranged on the other side of the holder; a pressing force maintaining means, including at least a torque limiter, arranged on the other side of the holder, for limiting to a predetermined value the pressing force with which the end portion of the rod member is pressed on the surface of the subject via the bag member; and a retracting mean including at least a torsion spring mechanism, arranged on the other side of the holder, for retracting the rod member when the end portion of the rod member receives a predetermined upward force from the surface of the subject via the bag member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENT

An embodiment of the present invention will now be described with reference to FIGS. 2 and 3.

Figure 2:
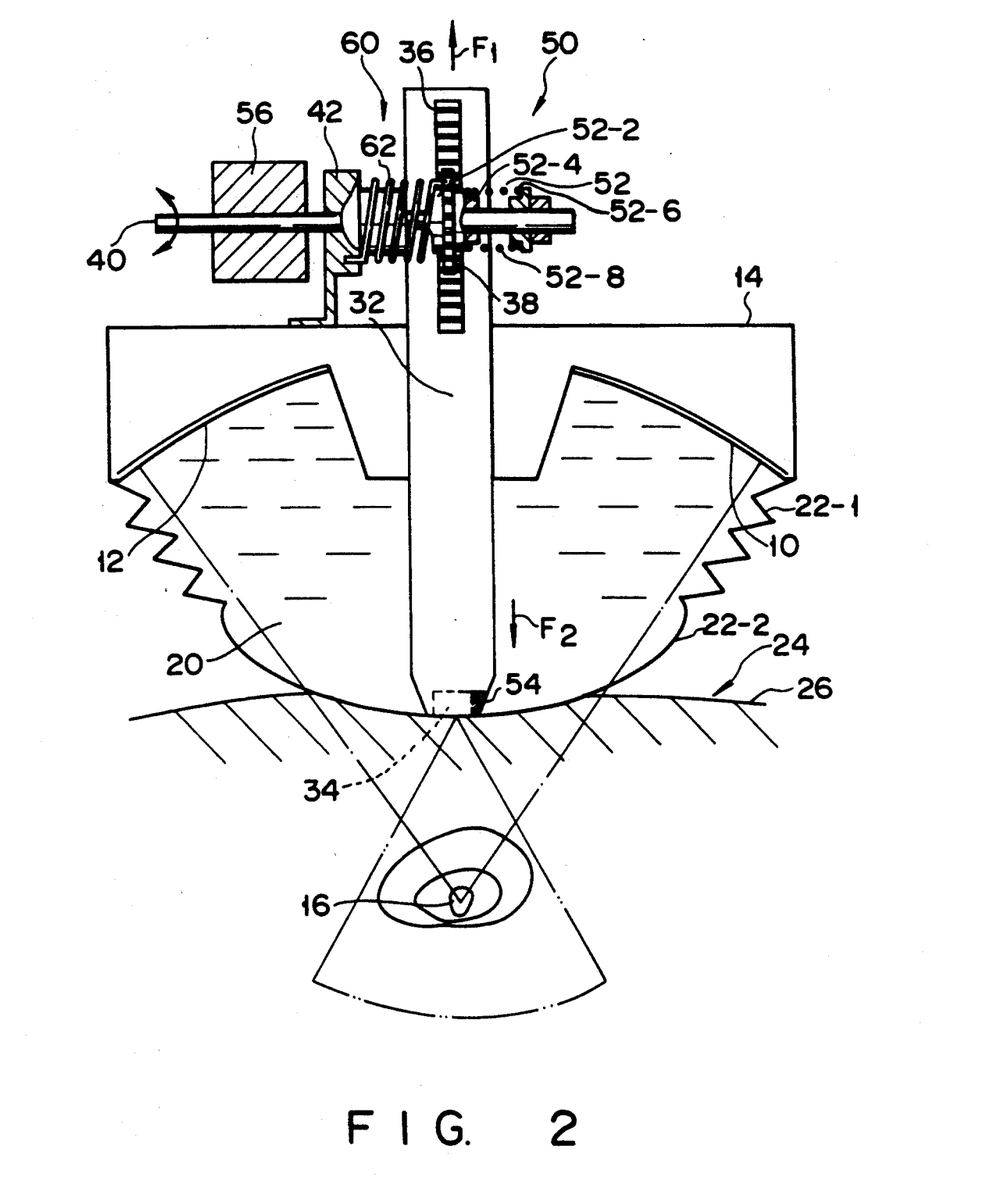
FIG. 2 is a cross-sectional view schematically showing a structure of an acoustic wave therapy apparatus according to an embodiment of the present invention.

In an acoustic wave therapy apparatus shown in FIG. 2, irradiation devices (as the acoustic wave generator) 10 and 12 for generating intense ultrasonic pulse waves or intense continuous ultrasonic waves are arranged on one side of a holder 14. A bellows 22-1 and a water bag 22-2, which constitute a bag member, are attached to the oscillators 10 and 12. The water bag 22-2 is put in contact with a surface 26 of a subject 24.

An advanceable/retractable probe rod 32 is arranged in the water bag 22-2 passing through a hole formed in the holder 14. An ultrasonic probe 34 for ultrasonic tomographic imaging is provided at an end portion of the probe rod 32.

Figure 3:
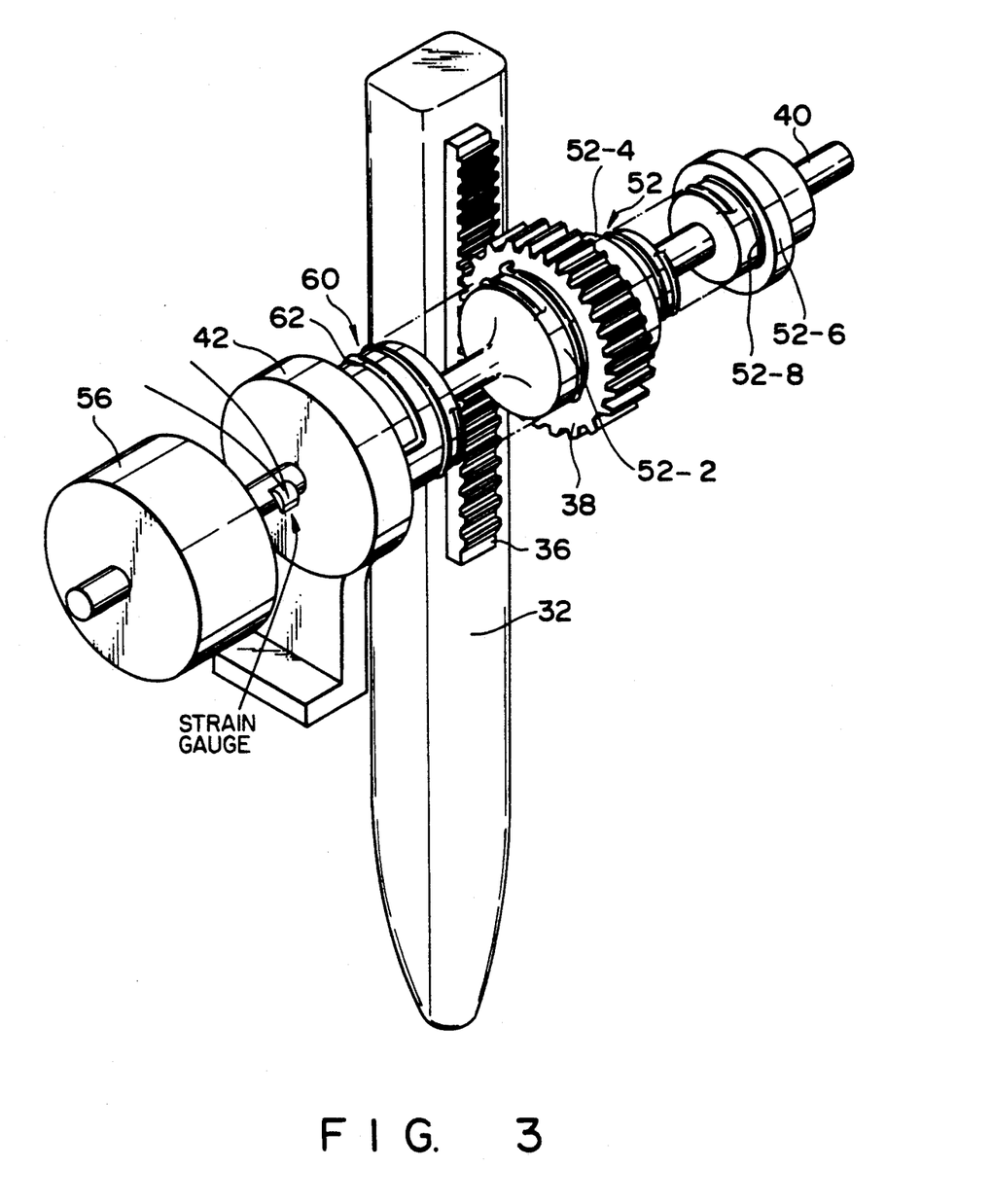
FIG. 3 is a perspective view showing a mechanical section mounted on a holder in the apparatus shown in FIG. 2.

As is shown in FIGS. 2 and 3, the probe rod 32 is provided with a rack gear 36 extending in the longitudinal direction of the probe rod 32. A pinion gear 38 engaging the rack gear 36, a gear drive shaft 40, and a bearing seat are arranged on the side of the holder 14, which is opposite to the side where the devices 10 and 12 are arranged.

In addition, a pressing force maintaining device 50 is provided for limiting to a predetermined value the pressure under which the end portion of the probe rod 32 is pressed on the surface 26 of the subject 24 via the water bag 22-2. There is also provided a retracting device 60 for retracting the probe rod 32 when the end portion of the probe rod 32 receives a predetermined pushing force from the surface 26 via the water bag 22-2.

The pressing force maintaining device 50 comprises a torque limiter 52, a pressure sensor 54, and a torque sensor 56.

The torque limiter 52 comprises a receiving plate 52-2 fixed on the drive shaft 40, a first plate 52-4 movably mounted on the drive shaft 40 to clamp the pinion gear between itself and the receiving plate 52-2, a second plate 52-6 fixed on the drive shaft 40 with a distance from the first plate 52-4, and a coil spring 52-8 mounted on the shaft 40 between the first plate 52-4 and the second plate 52-6. The pinion gear 38 arranged between the receiving plate 52-2 and the first plate 52-4 is clamped by means of the coil spring 52-8. This clamping force is equal to an upper limit value of the pressing force of the probe rod 32.

Thus, when the drive shaft 40 is rotated manually or by means of an electric mechanism, with a torque not higher than the upper limit value of the pressing force of the probe rod 32, the probe rod 32 can freely move vertically because the drive shaft 40, the receiving plate 52-2, the pinion gear 38, the first plate 52-4 and the second plate 52-6 rotate as one body.

On the other hand, when the drive shaft 40 is rotated with a torque higher than the upper limit value of the pressing force, the pinion gear 38 rotates idly though the drive shaft 40, the receiving plate 52-2, the first plate 52-4 and the second plate 52-6 rotate as one body.

More specifically, when the drive shaft 40 is rotated manually or by means of an electric mechanism, the torque higher than the upper limit value of the pressing force is not transmitted from the shaft 40 to the probe rod 32. Since a high pressing force is not applied to the subject 24 who is situated under the end portion of the probe rod 32, safety of the subject 24 is ensured. For the purpose of clear understanding, the operation of the torque limiter 52 of the maintaining device 50 has been described.

The pressure sensor 54 in the maintaining device 50 is provided at the end of the probe rod 32 or at the ultrasonic probe 34. The pressure sensor 54 senses the pressing force of the probe rod 32 and, when the sensed value exceeds a predetermined value, the sensor 54 indicates this fact, for example, by an alarm.

The torque sensor 56 is mounted on the drive shaft 40 and stops the rotation of the drive shaft 40 when the output from the sensor 56 exceeds a predetermined value. The maintaining device 50 may further include a strain gauge on the drive shaft 40, so that the rotation of the drive shaft 40 may be stopped when the output from the strain gauge exceeds a predetermined level.

In this embodiment, the retracting device 60 includes the aforementioned torsion spring 62. The torsion spring 62 is mounted on the drive shaft 40. The torsion spring 62 is fixed at one end to the bearing seat 42 and at the other end to the peripheral portion of the pinion gear 38. The torsion spring 62 lifts the probe rod 32 with an upward force F1 (indicated in FIG. 2). The upward force F1 is equivalent to the sum of the frictional force (acting upwards) between the probe rod 32 and the holder 14 and a downward force F2. The downward force F2 is produced by the weight of the probe rod 32, the ultrasonic probe 34 and the rack gear 36.

By virtue of this cancelling of upward and downward forces, the end portion of the probe rod 32 is allowed to contact with the surface 26 of the subject 24, with a suitable pressing force of, for example, 1 to 2 Kg.

The torsion spring 62 cancels the downward force F2 due to the weight of the probe rod 32, the ultrasonic probe 34 and the rack gear 36. Thus, the probe rod 32 is easily lifted by the force smaller than the force F2 and larger than the frictional force between the probe rod 32 and the holder 14, for example, when the subject 24 inhales and his/her belly swells. In this case, when no force is applied to the drive shaft 40, all of the drive shaft 40, the receiving plate 52-2, the pinion gear 38, the first plate 52-4 and the second plate 52-6 rotate as one body.

According to the apparatus having the above structure, when the drive shaft 40 is rotated with a torque exceeding a predetermined value, the excessive torque is not transmitted to the probe rod 32. Thus, the subject 24 is prevented from being injured, and the ultrasonic probe 34 is brought into contact with the surface 26 of the subject 24 under a suitable pressure. Therefore, excellent images can be obtained.

The pressure sensor 54 senses the pressing force of the probe rod 32. When the force sensed by the pressure sensor 54 exceeds a predetermined value, the operator's attention drawn to this fact by an alarm.

The torque sensor 56 senses the torque of the drive shaft 40, and, when the torque of the shaft 40 exceeds a predetermined value, the rotation of the drive shaft 40 is stopped. Thus, an excessive pressing force is not applied to the subject 24, and the subject 24 is prevented from being injured.

The torsion spring 62 is able to retract the probe rod 32 from the subject 24. When the probe rod 32 is put in contact with the subject 24, the torsion spring 62 limits the force with which the rod 32 is pressed on the subject 24. When the subject 24 moves upwards while the probe rod 32 is made to contact the subject 24, the probe rod 32 moves upwards. Thus, the subject 24 is prevented from being injured, and the safety for the subject 24 is ensured.

Figure 4:
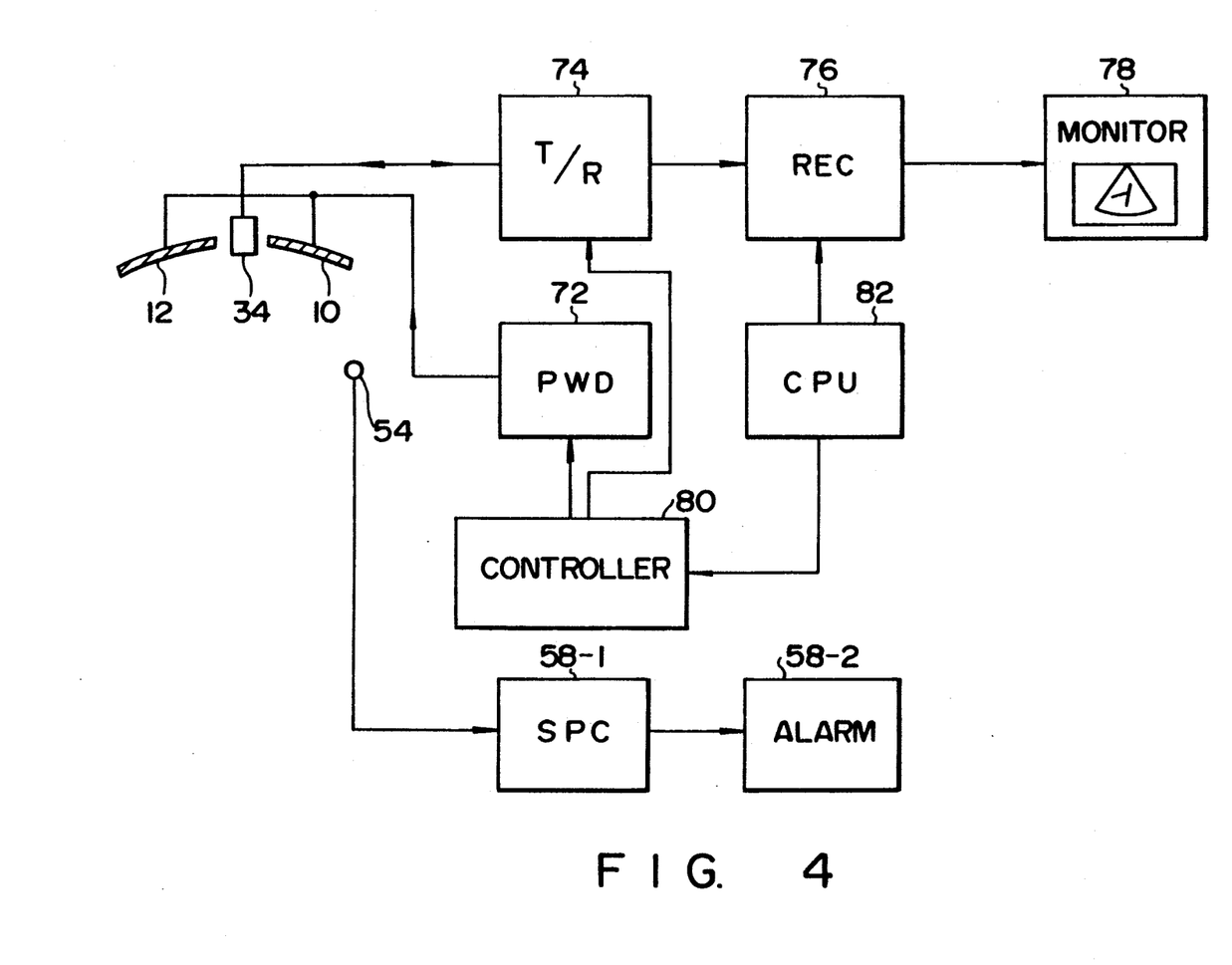
FIG. 4 is a block diagram illustrating an electric circuit in the case where the apparatus shown in FIG. 1 is employed as an ultrasonic shock wave lithotrity apparatus.

FIG. 4 is a block diagram for illustrating an electric circuit in the case where the apparatus shown in FIG. 1 is employed as an ultrasonic shock wave lithotrity apparatus. The irradiation devices 10 and 12 are driven by a pulse wave driver (PWD) 72 to radiate intense ultrasonic pulse waves. The ultrasonic probe 34 is driven by a transmitter/receiver (T/R) 74, and a received signal is sent to a reconstruction device (REC) 76, and the REC 76 produces, for example, tomograms. The produced tomograms are displayed on a monitor 78. A controller 80 controls the transmitter/receiver 74 and the pulse wave driver 72. The controller 80 receives commands from a CPU 82. The output from the pressure sensor 54 is applied to a signal processing circuit (SPC) 58-1. When the SPC 58-1 determines that the output from the pressure sensor 54 exceeds a predetermined level, an alarm 58-2 is driven to generate an alarm sound.

Figure 5:
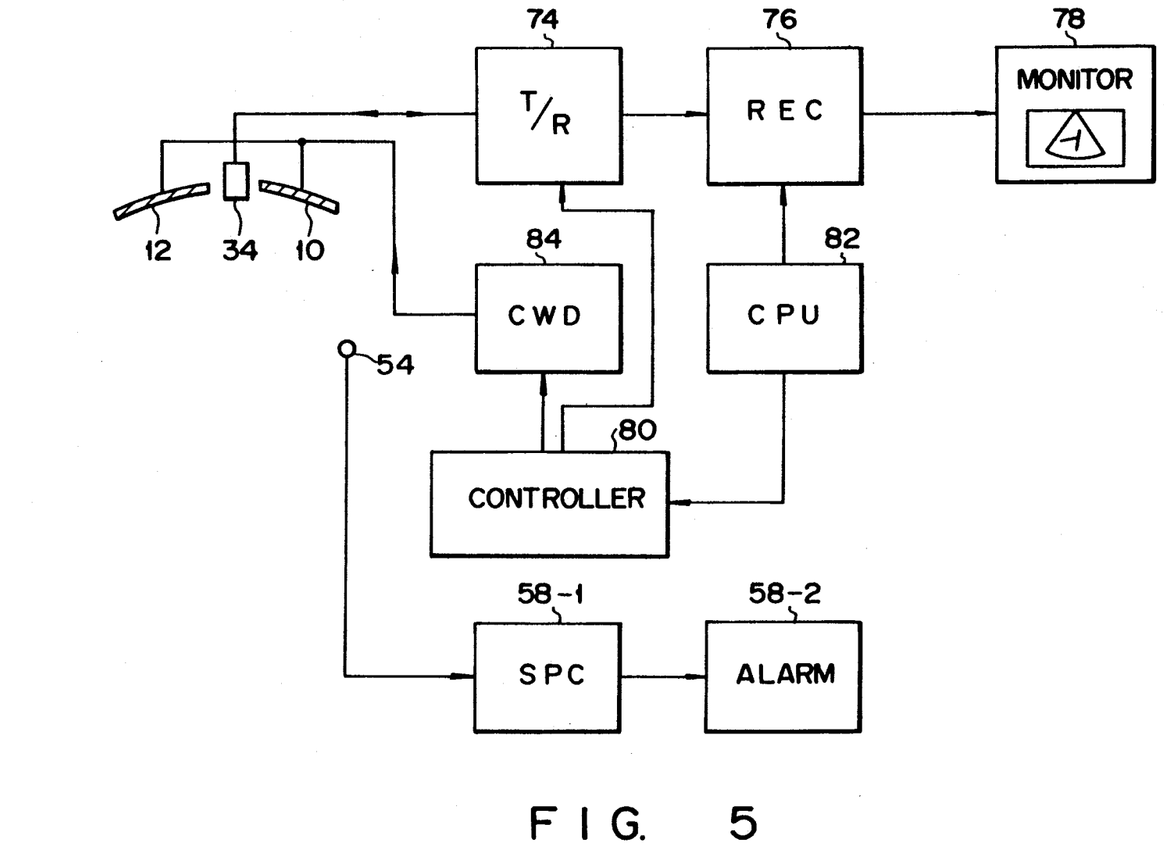
FIG. 5 is a block diagram illustrating an electric circuit in the case where the apparatus shown in FIG. 1 is employed as an ultrasonic continuous wave hyperthermic therapy apparatus.

FIG. 5 is a block diagram for illustrating an electric circuit in the case where the apparatus shown in FIG. 1 is employed as an ultrasonic continuous wave hyperthermic therapy apparatus. The irradiation devices 10 and 12 are driven by a continuous wave driver (CWD) 84 to generate intense continuous ultrasonic waves. The other structure is the same as that of the apparatus illustrated in FIG. 4.

Figure 6:
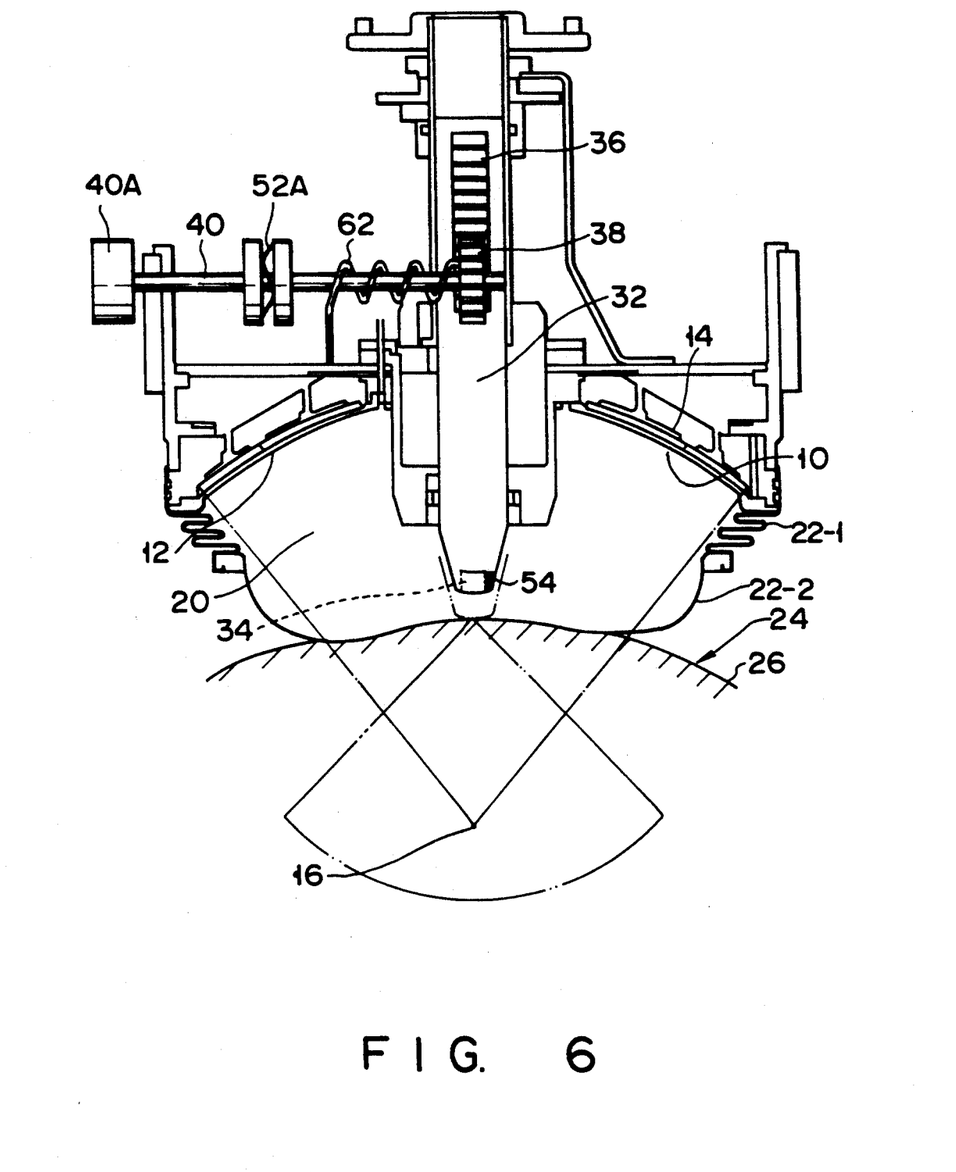
FIG. 6 is a cross-sectional view schematically showing a structure of an acoustic wave therapy apparatus according to another embodiment of the invention.

FIG. 6 is a cross-sectional view for schematically showing a structure of an acoustic wave therapy apparatus according to another embodiment of the invention. The structure of this apparatus is basically identical with that of the apparatus shown in FIG. 1 (and FIG. 2), except that a torque limiter 52A is provided at a middle portion of the drive shaft 40, and a manual knob 40A is provided at an end portion of the drive shaft 40.

As has been described above, the present invention provides an acoustic wave therapy apparatus ensuring the safety for the subject.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An acoustic wave therapy apparatus comprising:

a holder having a central portion, a one side portion and another portion, said one side portion including a concave surface and said central portion including a through-hole;

acoustic wave generating means, provided on said one side portion of said holder, for generating acoustic waves for medical treatment;

a bag member arranged on said one side portion of the holder and adapted to be put in contact with a surface of a subject, and containing an acoustic wave propagation medium;

a rod member having an end portion inserted into said through-hole of the holder and arranged to be vertically movable in said bag member, and adapted to be placed in contact with the surface of the subject through said bag member;

an ultrasonic probe for ultrasonic wave tomographic imaging, arranged on the end portion of the rod member;

a drive mechanism arranged on the other portion of the holder, for vertically moving the rod member within the through-hole relative to the holder; and a torque limiter provided on said drive mechanism for limiting to a predetermined value the pressing force with which the rod member is pressed on the subject.

2. The apparatus according to claim 1, further comprising a torque sensor, arranged on said drive mechanism, for sensing the torque acting on the drive mechanism and a stop mechanism for stopping said drive mechanism when the output from the torque sensor exceeds a predetermined level.

3. An acoustic wave therapy apparatus comprising:

a holder having a central portion, one side portion and another portion, said one side portion including a concave surface and said central portion including a through-hole;

acoustic wave generating means, provided on said one side portion of said holder, for generating acoustic waves for medical treatment;

a bag member arranged on said one side portion of the holder and adapted to be put in contact with a surface of a subject, and containing an acoustic wave propagation medium;

a rod member inserted into said through-hole of the holder and arranged to be vertically movable in said bag member, the rod member adapted to be placed in contact with the surface of the subject through said bag member;

an ultrasonic probe for ultrasonic wave tomographic imaging, provided on the rod member;

a drive mechanism, arranged on the other portion of the holder, for vertically moving the rod member within the through-hole relative to the holder; and retracting means provided on said drive mechanism, for retracting said rod member when the rod member receives a predetermined upward force from the subject.

4. The apparatus according to claim 3, wherein said acoustic wave generating means generates intense pulsed waves.

5. The apparatus according to claim 3, wherein said acoustic wave generating means generates intense continuous waves.

6. The apparatus according to claim 3, wherein said acoustic wave propagation medium is water.

7. The apparatus according to claim 3, wherein said retracting means is a torsion spring mechanism mounted on said drive mechanism.

8. An acoustic wave therapy apparatus comprising:

a holder having a central portion, one side portion and another portion, said one side portion including a concave surface and said central portion including a through-hole;

acoustic wave generating means, provided on said one side portion of said holder, for generating acoustic wave for medical treatment;

a bag member arranged on said one side portion of the holder and adapted to be put in contact with a surface of a subject, and containing an acoustic wave propagation medium;

a rod member inserted into said through-hole of the holder and arranged to be vertically movable in said bag member, and adapted to be placed in contact with the surface of the subject through said bag member;

an ultrasonic probe for ultrasonic wave tomographic imaging provided on the rod member;

a drive mechanism, arranged on the other portion of the holder, for vertically moving the rod member within the through-hole relative to the holder;

pressing force maintaining means provided on said drive mechanism for limiting to a predetermined value the pressing force with which the rod member is pressed on the subject; and retracting means, also provided on said drive mechanism for retracting said rod member when the rod member receives a predetermined upward force from the subject.

9. The apparatus according to claim 8, wherein said acoustic wave generating means generates intense pulsed waves.

10. The apparatus according to claim 8, wherein said acoustic wave generating means generates intense continuous waves.

11. The apparatus according to claim 8, wherein said acoustic wave propagation medium is water.

12. The apparatus according to claim 8, wherein said pressing force maintaining means comprises a pressure sensor for sensing the pressure acting on the rod member, and alarm means for indicating the fact that the output from the pressure sensor has exceeded a predetermined level.

13. The apparatus according to claim 8, wherein said pressing force maintaining means comprises a strain gauge mounted on said drive mechanism, and a stop mechanism for stopping the driving of said drive mechanism when the output from the strain gauge exceeds a predetermined level.

14. The apparatus according to claim 8, wherein said pressing force maintaining means comprises a torque sensor mounted on said drive mechanism, and a stop mechanism for stopping the driving of said drive mechanism when the output from the torque sensor exceeds a predetermined level.

15. The apparatus according to claim 8, wherein said retracting means is a torsion spring mechanism mounted on said drive mechanism.

16. An acoustic wave therapy apparatus comprising:

a holder having a central portion, a one side portion and another portion, said one side portion including a concave surface and said central portion including a through-hole acoustic wave generating means, provided on said one side portion of said holder, for generating acoustic waves for medical treatment;

a bag member arranged on said one side portion of the holder and adapted to be put in contact with a surface of a subject, and containing an acoustic wave propagation medium;

a rod member inserted into said through-hole of the holder and arranged to be advanceably and retractably moved in said bag member, and adapted to be placed in contact with the surface of the subject through said bag member;

an ultrasonic probe for ultrasonic wave tomographic imaging, provided at one end portion of the rod member;

a drive shaft member arranged on the other side portion of the holder, which is orthogonally extendible with respect to said rod member, a rack gear provided on said rod member, which is extendable with respect to said rod member;

a pinion gear engaged with said rack gear and provided on said drive shaft member, which is driven by said drive shaft member;

a bearing seat, fixed to the other side portion of said holder;

pressing force maintaining means including at least a torque limiter, provided on said drive shaft member for limiting to a predetermined value the pressing force with which the rod member is pressed on the subject said torque limiter comprises a receiving plate mounted on said drive shaft member, for receiving said pinion gear, a first plate rotatably arranged on said drive shaft member, for clamping said pinion gear between itself and the receiving plate, a second plate fixed on said drive shaft at a distance from first plate, and a coil spring provided on said drive shaft between said first plate and said second plate, having a force of tension equal to an upper limit value of the pressing force of said rod member; and retracting means including at least a torsion spring mechanism for lifting said rod member with an upward force which is equivalent to the sum of the frictional force between said rod member and said holder and a downward force which is produced by the weight of said rod member, said ultrasonic probe and said rack gear, provided on said drive shaft member for retracting said rod member when the rod member receives a predetermined upward force from the subject, said torsion spring mechanism comprises a coil spring passed over said drive shaft member, provided between said bearing seat and said pinion gear and having one end portion fixed on said bearing seat and the other end portion fixed on said pinion gear.

* * * * *